US 10,145,742 B1

(12) United States Patent
Lin et al.

(10) Patent No.: US 10,145,742 B1
(45) Date of Patent: Dec. 4, 2018

(54) PROBE COVER DISPENSING DEVICE

(71) Applicant: RADIANT INNOVATION INC., Hsinchu (TW)

(72) Inventors: Tseng-Lung Lin, Hsinchu (TW); Chin-Hui Ku, Hsinchu (TW)

(73) Assignee: RADIANT INNOVATION INC., Hsinchu (TW)

( * ) Notice: Subject to any disclaimer, the term of this patent is extended or adjusted under 35 U.S.C. 154(b) by 0 days.

(21) Appl. No.: 15/662,629

(22) Filed: Jul. 28, 2017

(51) Int. Cl.
| G01K 1/08 | (2006.01) |
| A61B 50/30 | (2016.01) |
| G01J 5/02 | (2006.01) |
| G01J 5/00 | (2006.01) |
| G01K 1/00 | (2006.01) |
| A61B 50/00 | (2016.01) |

(52) U.S. Cl.
CPC .............. *G01J 5/021* (2013.01); *A61B 50/30* (2016.02); *G01K 1/08* (2013.01); *A61B 50/00* (2016.02); *G01J 5/00* (2013.01); *G01K 1/00* (2013.01)

(58) Field of Classification Search
CPC ...................................................... G01J 5/021
USPC ............................. 221/92, 111, 112, 113, 115
See application file for complete search history.

(56) References Cited

U.S. PATENT DOCUMENTS

| 5,100,018 | A * | 3/1992 | Rosati ................ A61B 1/00142 |
| | | | 221/155 |
| 6,550,638 | B1 * | 4/2003 | Mochida ................ A47F 1/106 |
| | | | 221/124 |
| 8,418,880 | B2 * | 4/2013 | Yu ........................... G01J 5/021 |
| | | | 206/438 |
| 9,189,912 | B2 * | 11/2015 | Gunderson ............. G07F 13/10 |
| 9,520,256 | B2 * | 12/2016 | Naka ....................... H01H 50/04 |
| 2004/0016766 | A1 * | 1/2004 | Lin et al. |
| 2006/0222053 | A1 | 10/2006 | Babkes et al. |
| 2010/0032447 | A1 * | 2/2010 | Yu et al. |
| 2011/0299568 | A1 * | 12/2011 | Huang et al. |
| 2014/0117039 | A1 * | 5/2014 | Lin et al. |

FOREIGN PATENT DOCUMENTS

| CN | 102988029 A | 3/2013 |
| TW | I365281 A | 6/2012 |

* cited by examiner

*Primary Examiner* — Douglas A Hess
(74) *Attorney, Agent, or Firm* — Li & Cai Intellectual Propenv (USA) Office (57) ABSTRACT

The instant disclosure provides a probe cover dispensing device including a base and an elastic element. The base includes a housing unit, a probe cover dispensing unit and a connection unit disposed between the housing unit and the probe cover dispensing unit. The probe cover dispenser unit can rotate between a first predetermined position and a second predetermined position relative to the housing unit through the connection unit. The elastic element is disposed in the housing unit to apply a pressure on a probe cover which is disposed in the housing unit. The probe cover is abutted by the elastic element and limited in the housing unit. When the probe cover dispensing unit rotates from the first predetermined position to the second predetermined position, a sliding groove may be formed between the housing unit and the probe cover dispenser unit for the probe cover to slide therein.

10 Claims, 11 Drawing Sheets

PROBE COVER DISPENSING DEVICE

BACKGROUND

1. Technical Field

The instant disclosure relates to a probe cover dispensing device, and in particular, to a probe cover dispensing device adapted to probe covers of ear thermometer probes.

2. Description of Related Art

Existing probe cover dispensing devices generally have complicated structures, for example, Taiwan Patent No. 1365281 discloses a "probe cover dispensing device" which is an integrated device including a base having a probe cover groove, a probe cover housing groove for housing the probe cover, a gravity element for applying gravity to the probe cover in the probe cover housing groove and a pushing set disposed between the base and the probe cover housing groove. However, the device of the above patent has a complicated structure and a complicated operation procedure, presenting a significant disadvantage in manufacture and use. Meanwhile, the device is not portable and is hard to store.

In addition, U.S. Patent Publication No. 20060222053 discloses a "stackable tympanic thermometer probe cover cassette". Even if such a device can house a plurality of probe cover cassettes, the cost for manufacturing the device is too high, and the structure thereof is complicated.

SUMMARY

The object of the instant disclosure is to provide a probe cover dispensing device which is easy to use and easy to store.

In order to achieve the above object, an embodiment of the instant disclosure provides a probe cover dispensing device including a base and an elastic unit. The base includes a housing unit, a probe cover dispensing unit and a connection unit disposed between the housing unit and the probe cover dispensing unit. The probe cover dispensing unit rotates between a first predetermined location and a second predetermined location relative to the housing unit through the connection unit. The elastic unit is disposed in the housing unit for applying a pressure to a probe cover disposed in the housing unit. The probe cover is abutted by the elastic unit and limited in the housing unit. When the probe cover dispensing unit moves from the first predetermined location to the second predetermined location, a sliding groove for the probe cover to slide therein is formed between the housing unit and the probe dispensing unit.

One of the advantages of the instant disclosure is that the probe cover dispensing device provided by the embodiments of the instant disclosure is easy to use and easy to store based on the technical features of "a connection unit disposed between the housing unit and the probe cover dispensing unit for enabling the probe cover dispensing unit to rotate between a first predetermined location and a second predetermined location relative to the housing unit".

In order to further understand the techniques, means and effects of the instant disclosure, the following detailed descriptions and appended drawings are hereby referred to, such that, and through which, the purposes, features and aspects of the instant disclosure can be thoroughly and concretely appreciated; however, the appended drawings are merely provided for reference and illustration, without any intention to be used for limiting the instant disclosure.

BRIEF DESCRIPTION OF THE DRAWINGS

The accompanying drawings are included to provide a further understanding of the instant disclosure, and are incorporated in and constitute a part of this specification. The drawings illustrate exemplary embodiments of the instant disclosure and, together with the description, serve to explain the principles of the instant disclosure.

DESCRIPTION OF THE EXEMPLARY EMBODIMENTS

Reference will now be made in detail to the exemplary embodiments of the instant disclosure, examples of which are illustrated in the accompanying drawings. Wherever possible, the same reference numbers are used in the drawings and the description to refer to the same or like parts.

It should be noted that the following description uses the terms "first", "second", "third", etc. to describe various elements and signals. However, the elements and signals should not be limited by these terms. These terms are only use to distinguish one element or signal from another one. In addition, the term "or" can include one or more listed element based on actual implementation.

Reference is made to FIG. 1, FIG. 2, FIG. 7 and FIG. 8. The probe cover dispensing device U provided by the instant disclosure includes a base 1 and an elastic element 2 disposed in the base 1 (as shown in FIG. 3). The base 1 can include a housing unit 11, a probe cover dispensing unit 12 and a connection unit 13 disposed between the housing unit 11 and the probe cover dispensing unit 12. Comparing FIG. 1 and FIG. 7, the connection unit 13 can enable the rotation (pivotal rotation or swing) of the probe cover dispensing unit 12 relative to the housing unit 11 between a first predetermined location and a second predetermined location. In other words, when the probe cover dispensing unit 12 is located at the first predetermined location, the probe cover dispensing device U is in a storage state, and when the probe cover dispensing unit 12 is located at the second predetermined location, the probe cover dispensing device U is in a use state. During the use of the probe cover dispensing device U, a user can move a probe cover 3 from the housing unit 11 to the probe cover dispensing unit 12, then insert the probe of an ear thermometer (not shown) into the probe cover 3 on the probe cover dispensing unit 12 for fitting the probe cover 3 on the probe of the ear thermometer.

Figure 3:
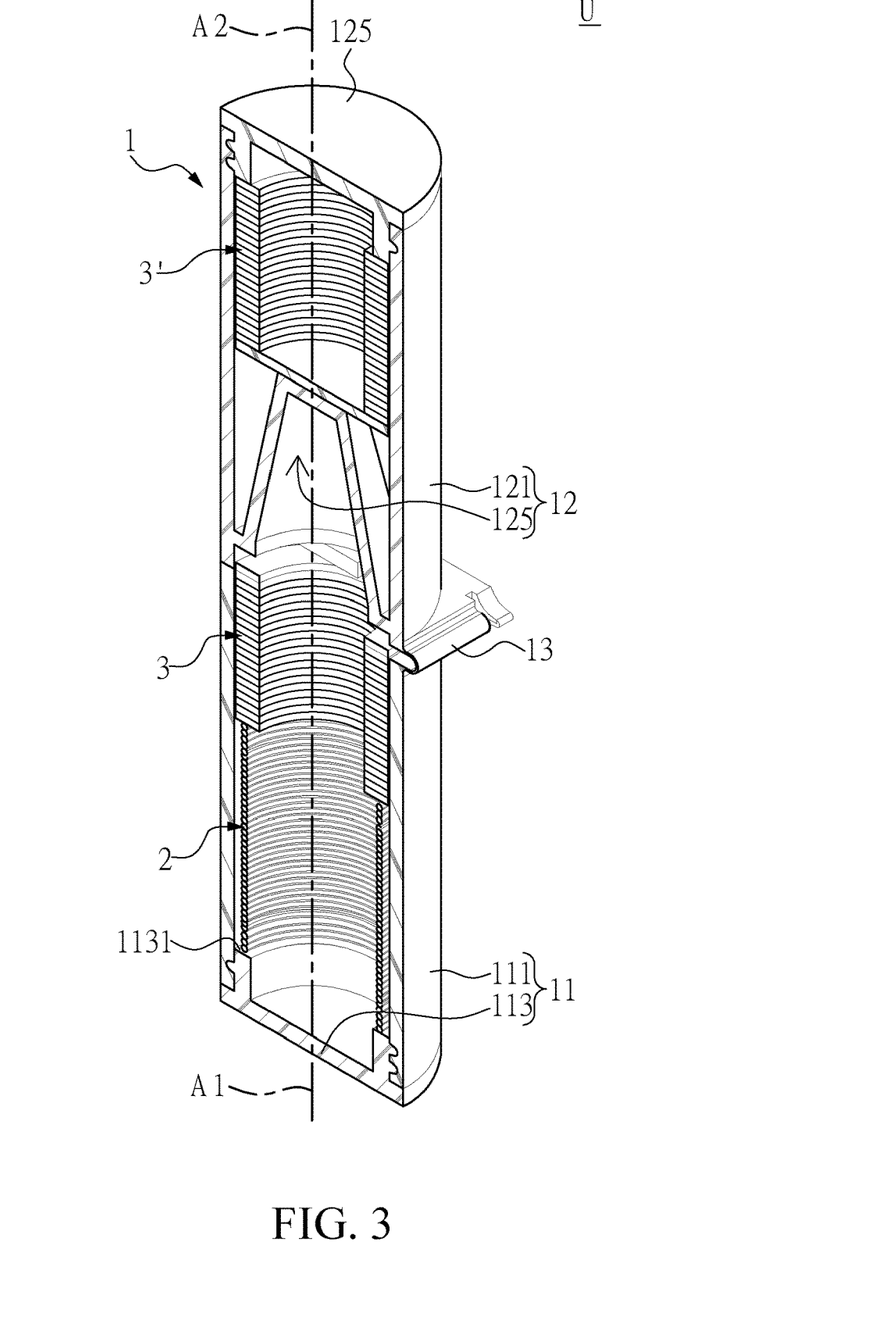
FIG. 3 is a three-dimensional assembled sectional view of the probe cover dispensing device provided by the embodiments of the instant disclosure.
Figure 4:
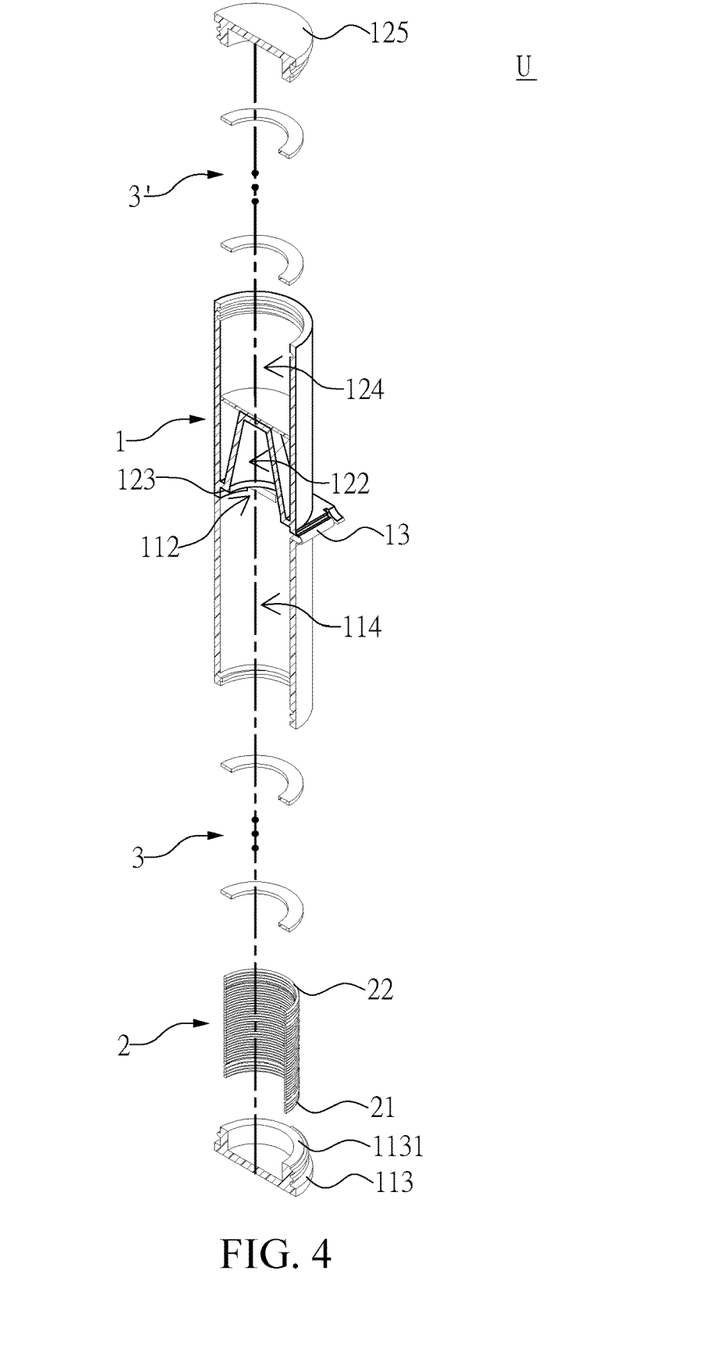
FIG. 4 is a three-dimensional exploded sectional view of the probe cover dispensing device provided by the embodiments of the instant disclosure.

Reference is made to FIG. 3 and FIG. 4. The specific structure of the probe cover dispensing device U is described below. For example, the connection unit 13 can be disposed integrally with the housing unit 11 and the probe cover dispensing unit 12. In the embodiments of the instant disclosure, the housing unit 11, the probe cover dispensing unit 12 and the connection unit 13 can be made of plastic such as polymer materials (for example, polypropylene (PP)). However, the instant disclosure is not limited thereto. Therefore, the connection unit 13 can be flexible and therefore enable the probe cover dispensing unit 12 to rotate between the first predetermined location and the second predetermined location relative to the housing unit 11. In addition, it should be noted that in other embodiments, the connection unit 13 can be a pivot axis or a hinge. The instant disclosure is not limited thereto.

Figure 9:
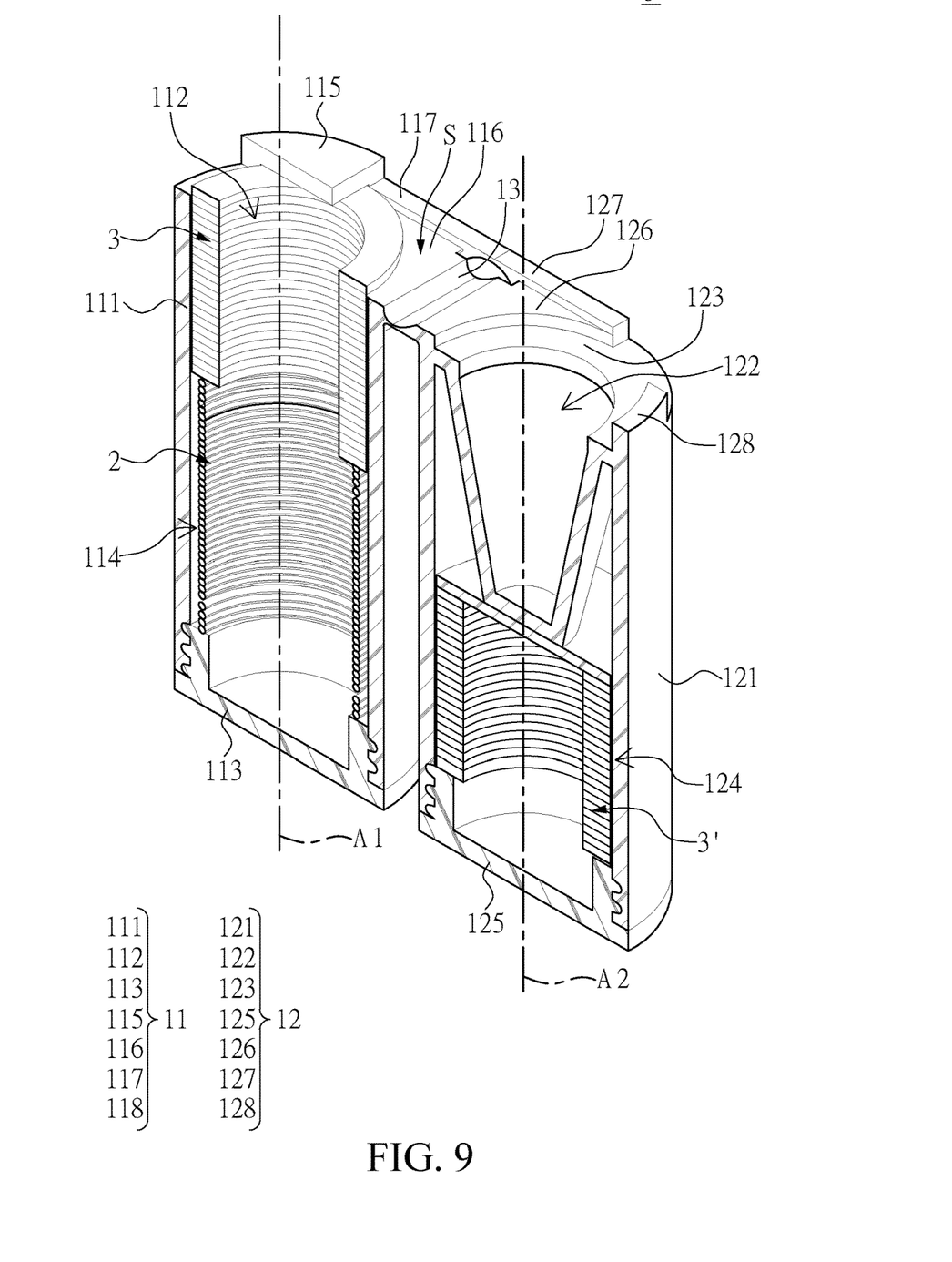
FIG. 9 is a three-dimensional sectional view of the probe cover dispensing device provided by the embodiments of the instant disclosure in a state of use.
Figure 10:
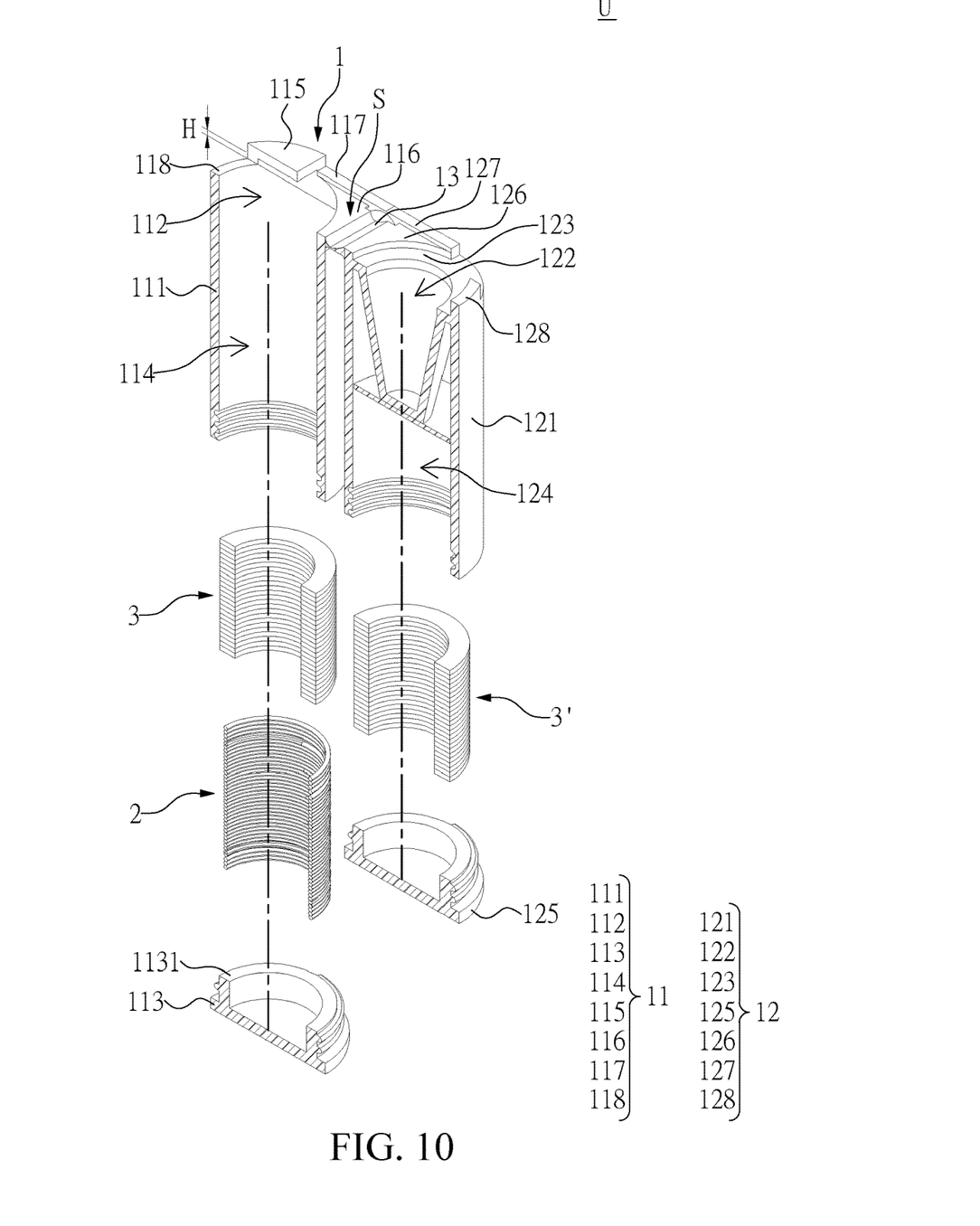
FIG. 10 is a three-dimensional exploded sectional view of the probe cover dispensing device provided by the embodiments of the instant disclosure.

Reference is now made to FIG. 9 and FIG. 10. For example, the housing unit 11 can be a hollow tube for housing the elastic element 2 and a plurality of probe covers 3. The elastic element 2 can be disposed in the housing unit 11 for applying a pressure (a force) to one or a plurality of probe covers 3 disposed in the housing unit 11, and the probe covers 3 can be abutted by the elastic element 2 and limited in the housing unit 11. Specifically, the housing unit 11 can include a housing body 111, an opening end 112 located on the housing body 111, an abutting end 1131 opposite to the opening end 112 and disposed on the housing body 111, a housing space 114 connected between the opening end 112 and the abutting end 1131 and a stopping portion 115 adjacent to the opening end 112 and located on the housing body 111. The elastic element 2 and the plurality of probe covers 3 can be disposed in the housing space 114, and the plurality of probe covers 3 can be disposed between the elastic element 2 and the stopping portion 115.

As shown in FIG. 3, FIG. 4, FIG. 9 and FIG. 10, the elastic element 2 can include a first side end 21 and a second side end 22 corresponding to the first side end 21. The first side end 21 of the elastic element 2 can abut the abutting end 1131 located at one side of the housing space 114. The second side end 22 can abut a probe cover 3 for abutting the probe cover 3 on the stopping portion 115, thereby limiting the probe covers 3 inside the housing space 114 of the housing unit 11. For example, the elastic element 2 can be a compression spring which applies a pressure on the plurality of probe covers 3. However, the instant disclosure is not limited thereto.

The housing unit 11 can further include a first cover 113 which has the abutting end 1131. In other words, the first cover 113 is detachably disposed on the bottom portion of the housing body 111 for sealing an end of the housing space 114. Meanwhile, the first cover 113 can be used as the opening for filling the probe covers 3. In addition, it should be noted that although the above description includes using the elastic element 2 to abut the abutting end 1131 of the first cover 113, in other embodiments, the opening for filling the probe covers 3 can be formed on a side surface of the housing body 111 and the first cover 113 can be disposed on the side surface of the housing body 111. In addition, the bottom portion of the housing body 111 can be a sealed end for forming the abutting end 1131 on which the first side end 21 of the elastic element 2 is abutted. However, the instant disclosure is not limited by the form of the abutting end 1131 or the form of the opening for filling the probe covers 3. It should be noted that an external thread (not labeled) can be formed on the first cover 113 for matching the internal thread (not labeled) on the bottom of the housing body 111, and hence, the first cover 113 can be disposed on the housing body 111. However, the manner of connection between the first cover 113 and the housing body 111 is not limited in the instant disclosure.

As shown in FIG. 3, FIG. 4, FIG. 9 and FIG. 10, the probe cover dispensing unit 12 can include a probe cover dispensing body 121, a probe cover dispensing slot 122 disposed on the probe cover dispensing body 121 and a probe cover limiting groove 123 disposed on the probe cover slot 122. For example, the shape of the probe cover slot 122 can be substantially the same as the probe of the ear thermometer for enabling the probe of the thermometer to insert into the probe cover slot 122. In addition, the shape of the probe cover limiting groove 123 is substantially the same as the contours of a probe cover 3 so as to enable the probe covers 3 to be limited therein. Preferably, the probe cover dispensing unit 12 further includes a backup housing area 124 disposed in the probe cover dispensing body 121, which can be used to house a plurality of backup probe covers 3'. The probe cover dispensing unit 12 further includes a second cover 125 adjacent to the backup housing area 124 and disposed on the bottom of the probe cover dispensing body 121 for sealing the backup housing area 124. It should be noted that the second cover 125 can have an external thread (not labeled) corresponding to an internal thread (not labeled) on the probe cover dispensing body 121 for disposing the second cover 125 on the probe cover dispensing body 121. However, the manner of connection between the second cover 125 and the probe cover dispensing body 121 is not limited in the instant disclosure.

Figure 5:
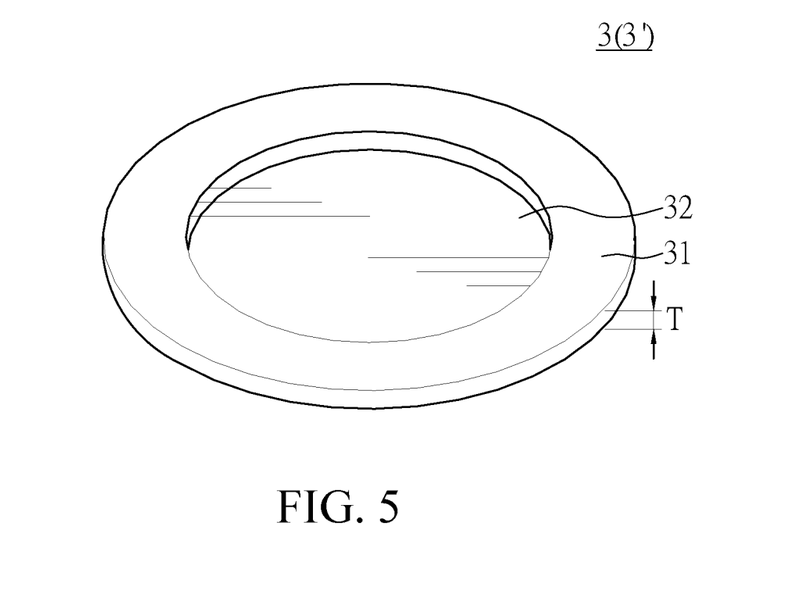
FIG. 5 is a three-dimensional schematic view of a probe cover of the embodiments of the instant disclosure.
Figure 6:
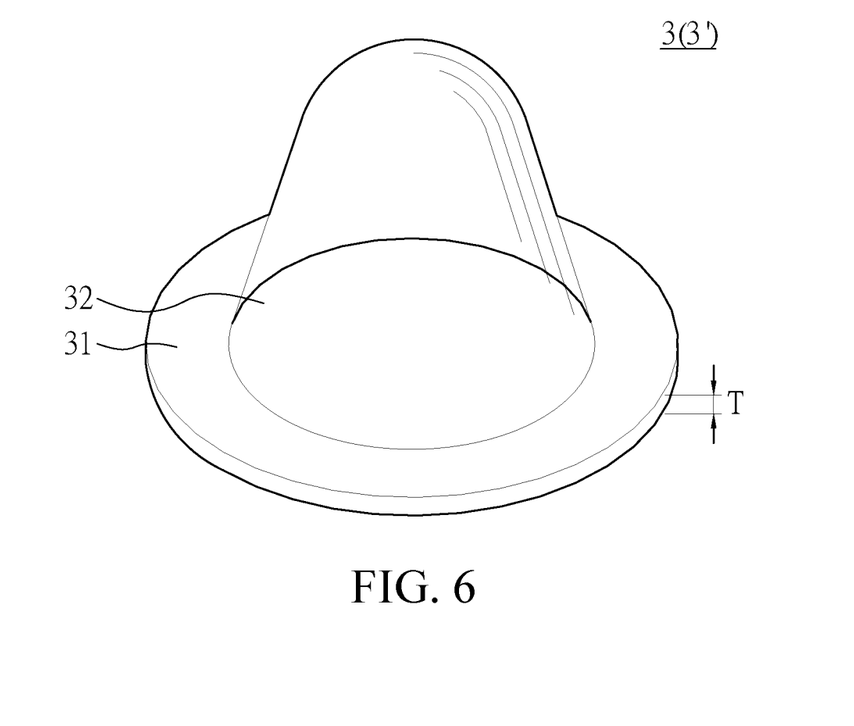
FIG. 6 shows another probe cover of the embodiments of the instant disclosure.

Reference is made to FIG. 5 and FIG. 6. The specific structure and shape of a probe cover 3 is described in detail below. For example, the probe cover 3 can include a frame 31 and a shield 32 connected to the frame 31. The shield 32 can be a soft film material which is foldable and flexible for being surrounded by the frame 31. Therefore, as shown in FIG. 5, the folded probe cover 3 can be substantially flat and a plurality of probe covers 3 can be stacked sequentially in the housing space 114 of the backup housing area 124. As shown in FIG. 6, the shield 32 of the unfolded probe cover 3 can extend and have a shape substantially the same as that of the thermometer probe. It should be noted that in order to keep the illustrations simple and clear, the probe cover 3 shown in figures other than FIGS. 5 and 6 are depicted only by the frame 31.

Reference is now made to FIG. 9 and FIG. 10. The housing unit 11 can further include a first end surface 116 adjacent to the opening end 112 and disposed on the housing body 111, and a first limiting projection 117 connected to the first end surface 116 and disposed on the housing body 111.

In addition, the probe cover dispensing unit 12 further includes a second end surface 126 adjacent to the probe cover limiting groove 123 and a second limiting projection 127 connected to the second end surface 126 and disposed on the probe cover dispensing body 121. Therefore, when the probe cover dispensing unit 12 moves from the first predetermined location to the second predetermined location, a sliding groove S for the probe cover 3 to slide is formed between the housing unit 11 and the probe cover dispensing unit 12.

As shown in FIG. 9 and FIG. 10, the sliding groove S can be formed by the first end surface 116, the second end surface 126, the first limiting projection 117 and the second limiting projection 127. In other words, as shown in FIG. 9, when the probe cover dispensing unit 12 moves from the first predetermined location to the second predetermined location, the first end surface 116 of the housing unit 11 and the second end surface 126 of the probe cover dispensing unit 12 can form a co-plane for the probe cover 3 to slide thereon. Meanwhile, the first limiting projection 117 of the housing unit 11 and the second limiting projection 127 of the probe cover dispensing unit 12 can surround the co-plane formed by the first end surface 116 and the second end surface 126 for limiting the moving direction of the probe cover 3.

Furthermore, as shown in FIG. 3 and FIG. 10, the housing unit 11 can include a first central axis A1 and the probe cover dispensing unit 12 can include a second central axis A2. When the probe cover dispensing unit 12 is located at the first predetermined location, the first central axis A1 and the second central axis A2 are parallel to each other. Preferably, the first central axis A1 and the second central axis A2 can be co-axial for forming a column. However, the instant disclosure is not limited thereto. Therefore, the probe cover dispensing device U provided by the instant disclosure can form a column which is easy to store or carry. It should be noted that in other embodiments, the probe cover dispensing unit 12 can include only the probe cover dispensing body 121, the probe cover slot 122, the probe cover limiting groove 123, the second end surface 126 and the second limiting projection 127, and hence, the size of the probe cover dispensing unit 12 can be smaller than that of the housing unit 11. Furthermore, when the probe cover dispensing unit 12 is located at the second predetermined location, the first central axis A1 and the second central axis A2 can have a distance therebetween and be parallel to each other, thereby forming a co-plane by the first end surface 116 of the housing unit 11 and the second end surface 126 of the probe cover dispensing unit 12 so that the probe cover 3 can move (slide) thereon.

Reference is made to FIG. 5 and FIG. 10. The first end surface 116 and the stopping portion 115 of the housing unit 11 can have a predetermined height H therebetween. The predetermined height H can be larger than or equal to a predetermined thickness T of the probe cover 3. Therefore, by moving the probe cover 3, the probe cover 3 can move from the first end surface 116 of the housing unit 11 to the second end surface 126 of the probe cover dispensing unit 12.

In addition, as shown in FIG. 3 and FIG. 4, when the probe cover dispensing unit 12 moves from the second predetermined location to the first predetermined location, the first end surface 116 of the housing unit 11 and the second end surface 126 of the probe cover dispensing unit 12 can be opposite to each other (facing each other), and the first end surface 116 and the second end surface 126 can have a distance therebetween. In addition, the first limiting projection 117 of the housing unit 11 and the second limiting projection 127 of the probe cover dispensing unit 12 can be opposite to each other or overlapped with each other to render the probe cover dispensing device U as a column which is easy to store or carry.

Figure 2:
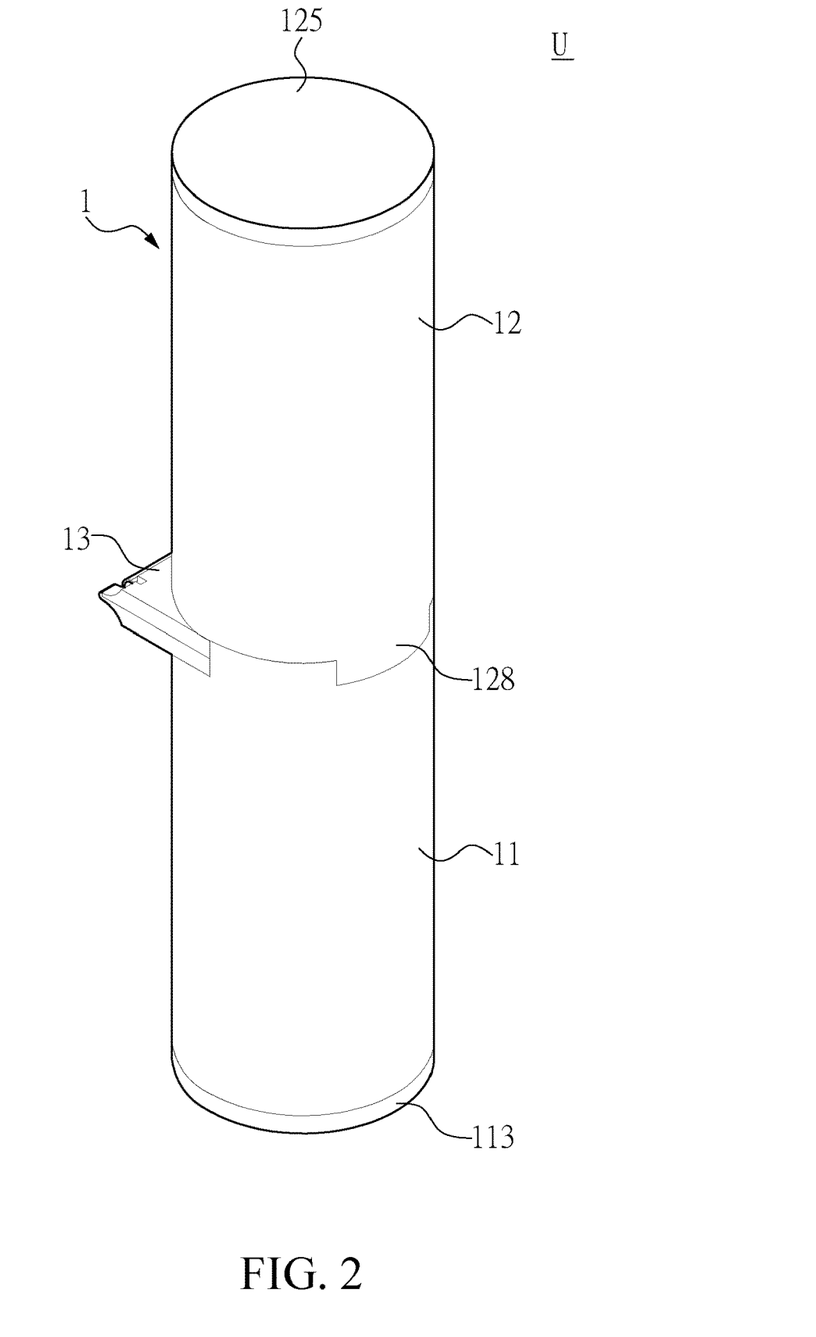
FIG. 2 is another three-dimensional assembled schematic view of the probe cover dispensing device provided by the embodiments of the instant disclosure.
Figure 8:
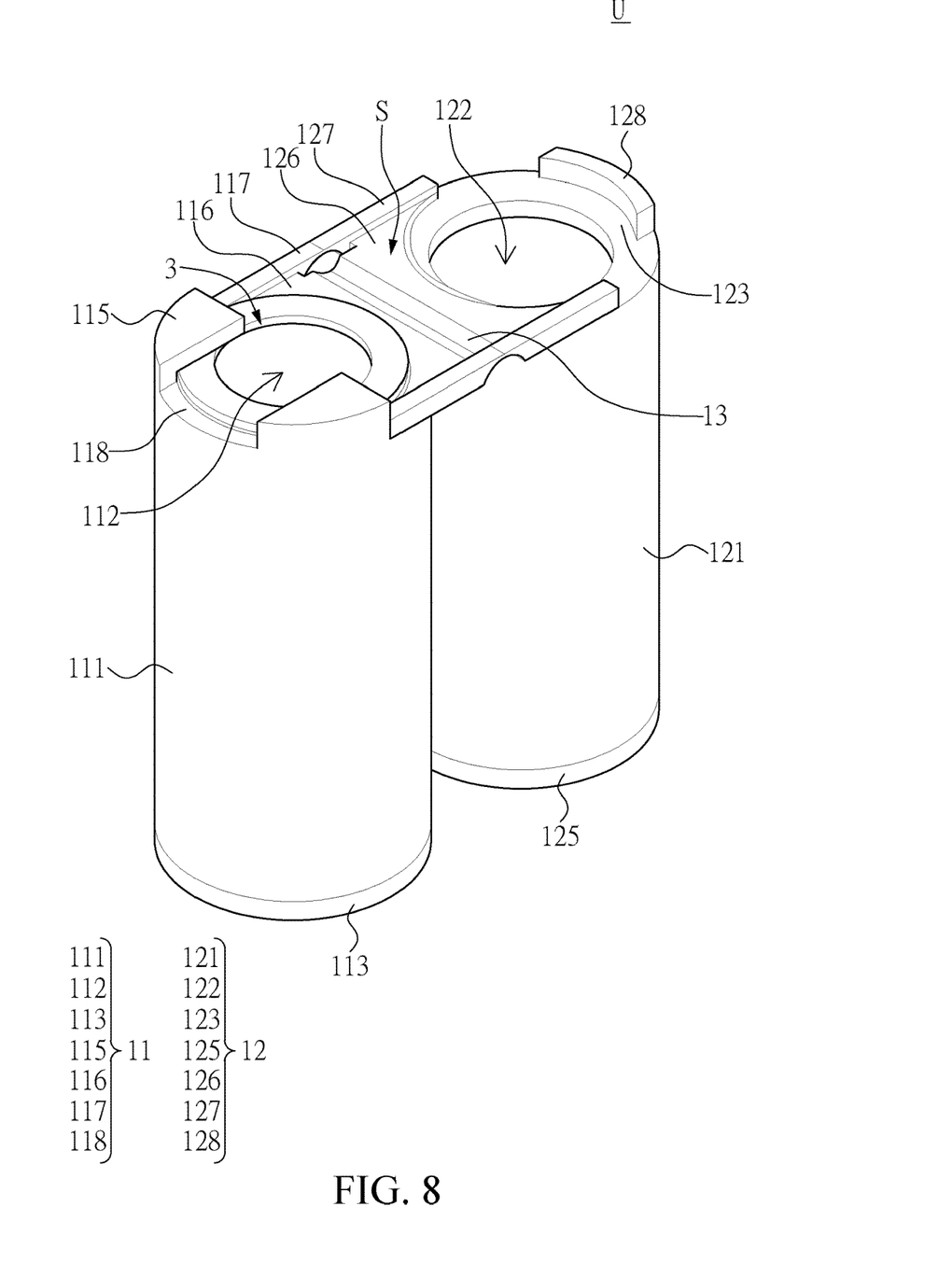
FIG. 8 is another three-dimensional schematic view of the probe cover dispensing device provided by the embodiments of the instant disclosure in a state of use.

It should be noted that as shown in FIG. 2 an FIG. 8, in the embodiments of the instant disclosure, the base 1 can further include a first connection portion 118 disposed on the housing unit 11 and a second connection portion 128 disposed on the probe cover dispensing unit 12. The first connection portion 118 and the second connection portion 128 can correspond to each other in shape/position. The housing unit 11 and the probe cover dispensing unit 12 are connected to each other through the first connection portion 118 and the second connection portion 128. For example, the first connection portion 118 can be a groove formed between the two stopping portions 115 of the housing unit 11, and the second connection portion 128 can be a projection (a bump) projected from the second end surface 126 of the probe cover dispensing unit 12. The groove of the housing unit 11 (the first connection portion 118) can be engaged with the projection of the probe cover dispensing unit 12 (the second connection portion 128) for limiting the probe cover dispensing unit 12 on a first predetermined location. It should be noted that in other embodiments, the manner of connection between the first connection portion 118 and the second connection portion 128 is not limited to that involving a groove and a projection. For example, the probe cover dispensing unit 12 can be positioned on the first predetermined location by means of fitting, buckling or magnetic connection. The manner of connection between the first connection portion 118 and the second connection portion 128 is not limited in the instant disclosure.

Figure 1:
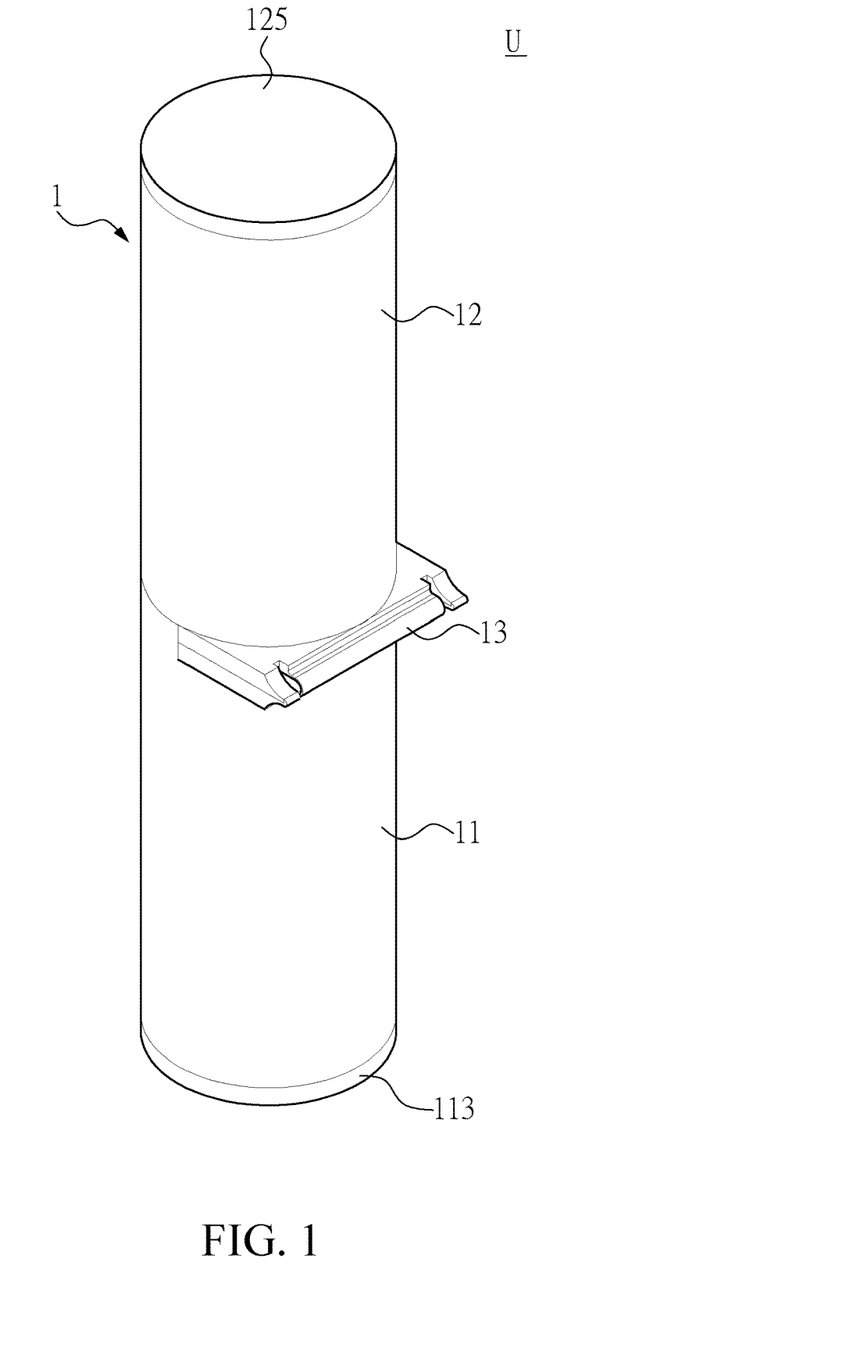
FIG. 1 is a three-dimensional assembled schematic view of the probe cover dispensing device provided by the embodiments of the instant disclosure.
Figure 7:
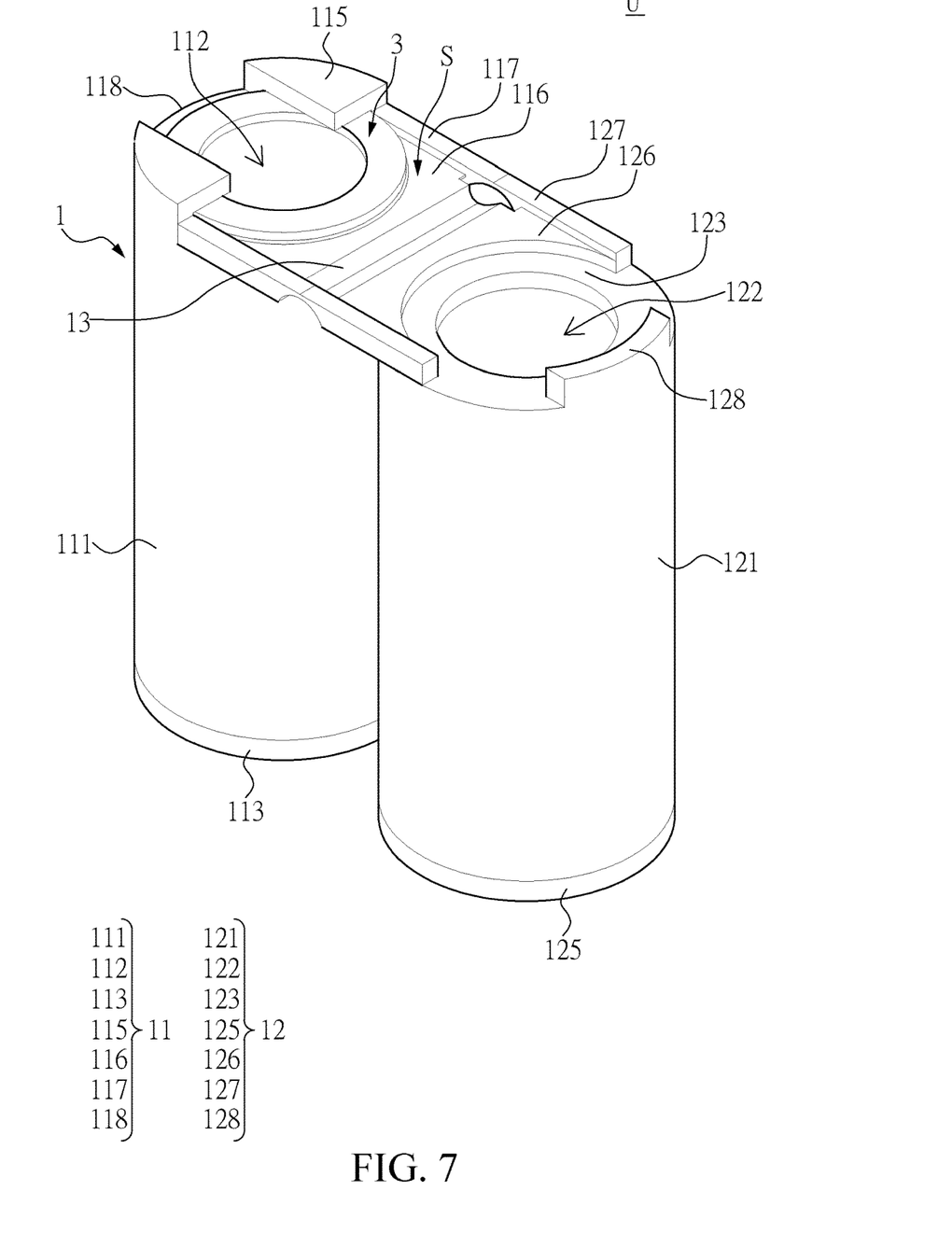
FIG. 7 is a three-dimensional schematic view of the probe cover dispensing device provided by the embodiments of the instant disclosure in a state of use.
Figure 11:
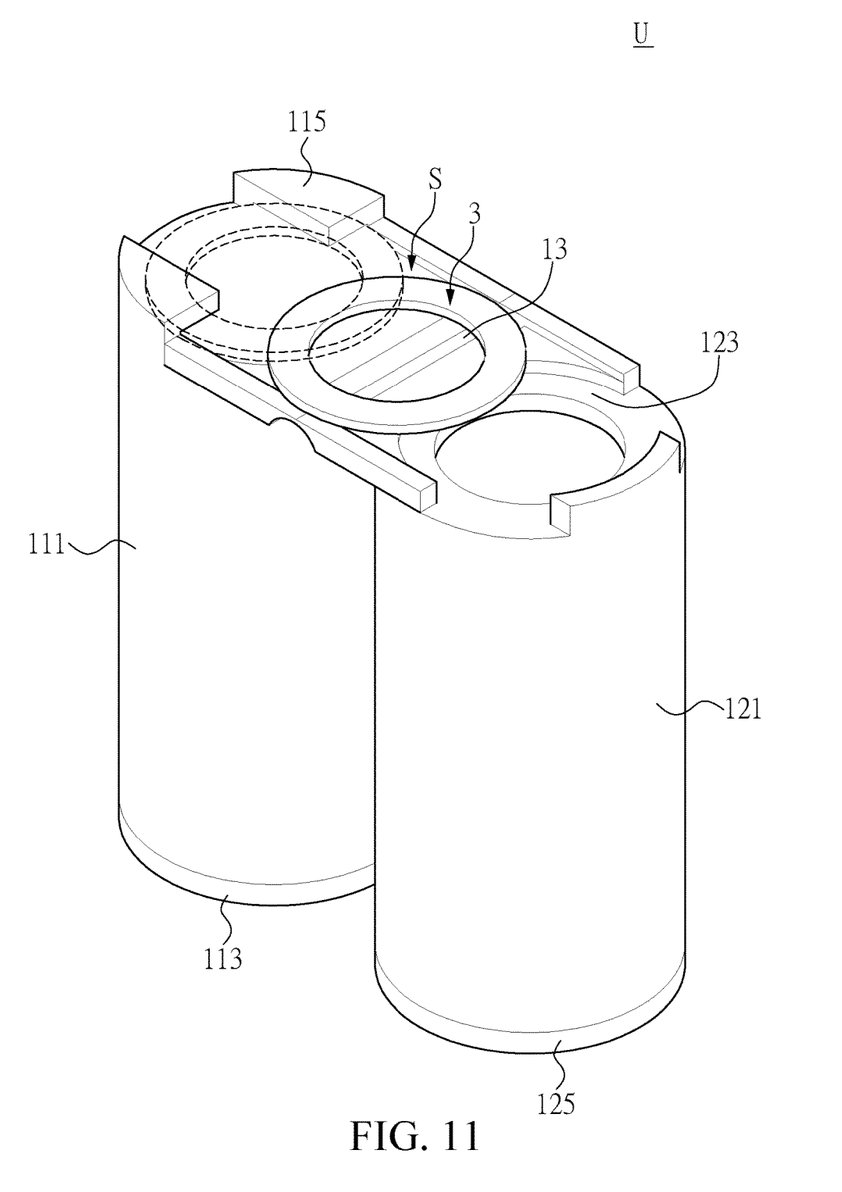
FIG. 11 is a three-dimensional schematic view showing the movement of the probe cover achieved by the probe cover dispensing device provided by the embodiments of the instant disclosure.
Figure 12:
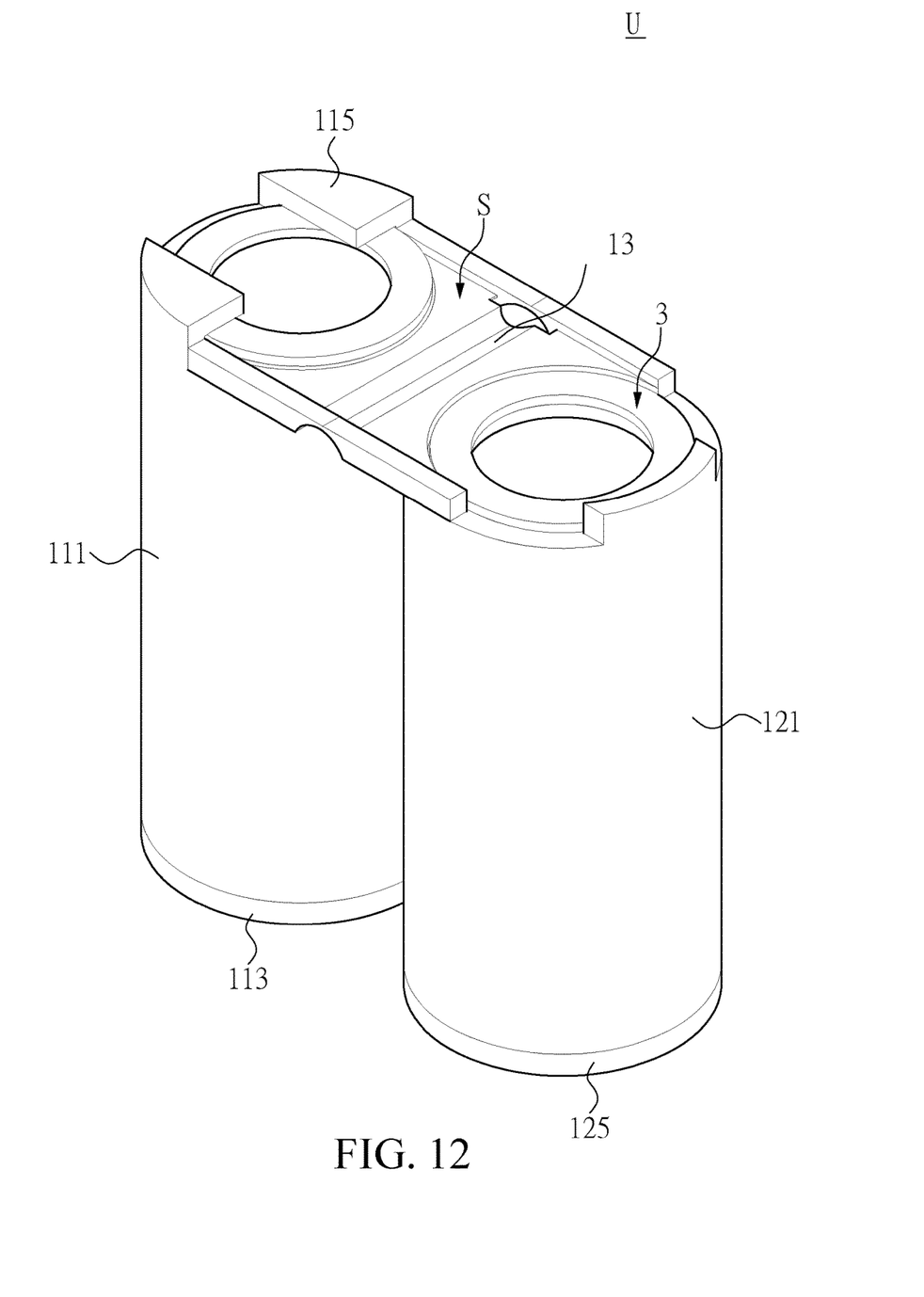
FIG. 12 is another three-dimensional schematic view showing the movement of the probe cover achieved by the probe cover dispensing device provided by the embodiments of the instant disclosure.

Reference is made to FIG. 7, FIG. 11 and FIG. 12. The movement of the probe cover 3 is described below. For example, as shown in FIG. 7 and FIG. 11, when a user moves the probe cover dispensing unit 12 to the second predetermined location, in order to put the probe cover 3 on the probe of the thermometer (for example, an ear thermometer) without touching the probe cover 3 by the user's hand, the user can move a probe cover 3 on the housing unit 11 to the sliding groove S by the probe of the thermometer. Next, as shown in FIG. 12, the user continues to move the probe cover 3 along the sliding groove S to the probe cover limiting groove 123 of the probe cover dispensing unit 12. Therefore, the probe cover 3 can be limited inside of the probe cover limiting groove 123. The probe of the thermometer can then insert into the probe cover 3 on the probe cover dispensing unit 12. Since the frame 31 of the probe cover 3 is abutted on the probe cover limiting groove 123 and the shield 32 of the probe cover 3 is folded and flexible, the probe of the thermometer can enter into the shield 32 and have the probe cover 3 positioned on the probe of the thermometer. Afterward, as shown in FIG. 1, once the probe cover 3 is taken and used, the probe cover dispensing unit 12 of the probe cover dispensing device U can be moved to the first predetermined location for turning the probe cover dispensing device U into a column, thereby storing the probe cover dispensing device U and saving space.

One of the advantages of the instant disclosure is that the probe cover dispensing device U provided by the instant disclosure is easy to use and easy to store based on the technical features of "a connection unit 13 disposed between the housing unit 11 and the probe cover dispensing unit 12 for enabling the probe cover dispensing unit 12 to rotate between a first predetermined location and a second predetermined location relative to the housing unit 11".

Specifically, since the probe cover dispensing unit 12 can rotate between the first predetermined location and the second predetermined location relative to the housing unit 11, the structure of the probe cover dispensing unit 12 is not only simple and includes less components, the object of easy to store and easy to carry can be achieved. In addition, the backup housing area 124 can house a plurality of backup probe covers 3' for providing sufficient probe covers 3 for use.

The above-mentioned descriptions represent merely the exemplary embodiment of the instant disclosure, without any intention to limit the scope of the instant disclosure thereto. Various equivalent changes, alterations or modifications based on the claims of the instant disclosure are all consequently viewed as being embraced by the scope of the instant disclosure.

What is claimed is:

1. A probe cover dispensing device, comprising:
   a base, the base including a housing unit, a probe cover dispensing unit and a connection unit disposed between the housing unit and the probe cover dispensing unit, wherein the probe cover dispensing unit rotates between a first predetermined location and a second predetermined location relative to the housing unit through the connection unit; and
   an elastic unit disposed in the housing unit for applying a pressure to a probe cover disposed in the housing unit, the probe cover being abutted by the elastic unit and limited in the housing unit;
   wherein when the probe cover dispensing unit moves from the first predetermined location to the second predetermined location, a sliding groove for the probe cover to slide therein is formed between the housing unit and the probe dispensing unit.

2. The probe cover dispensing device according to claim 1, wherein the housing unit includes a housing body, an opening end located on the housing body, an abutting end opposite to the opening end and located on the housing body, a housing space connected to the opening end and a stopping portion adjacent to the opening end, wherein the probe cover is disposed between the elastic unit and the stopping portion.

3. The probe cover dispensing device according to claim 2, wherein the housing unit further includes a first cover having the abutting end.

4. The probe cover dispensing device according to claim 2, wherein the elastic unit includes a first end portion and a second end portion corresponding to the first end portion, the first end portion abutting the abutting end, the second end portion abutting the probe cover for enabling the probe cover to abut the stopping portion and be limited inside the housing unit.

5. The probe cover dispensing device according to claim 2, wherein the probe dispersing unit includes a probe cover dispensing body, a probe cover slot located on the probe cover dispensing body and a probe cover limiting groove disposed on the probe cover slot, wherein when the probe cover dispensing unit is located at the second predetermined location, the probe cover can move into the probe cover limiting groove through the sliding groove.

6. The probe cover dispensing device according to claim 5, wherein the probe cover dispensing unit further includes a backup housing area disposed in the probe cover dispensing body, the backup housing area is configured to house a plurality of backup probe covers.

7. The probe cover dispensing device according to claim 6, wherein the probe cover dispensing unit further includes a second cover disposed adjacent to the backup housing area for sealing the backup housing area.

8. The probe cover dispensing device according to claim 1, wherein the housing unit further includes a first end surface and a first limiting projection connected to the first end surface, the probe cover dispensing unit further including a second end surface and a second limiting projection connected to the second end surface, the sliding groove being formed by the first end surface, the second end surface, the first limiting projection and the second limiting projection.

9. The probe cover dispensing device according to claim 1, wherein the base further includes a first connection portion disposed on the housing unit and a second connection portion disposed on the probe cover dispensing unit, the first connection portion and the second connection portion are disposed corresponding to each other, and the housing unit and the probe cover dispensing unit are connected to each other through the coordination of the first connection portion and the second connection portion.

10. The probe cover dispensing device according to claim 1, wherein the connection unit is flexible.

* * * * *